United States Patent [19]

Marhold et al.

[11] Patent Number: 4,885,415

[45] Date of Patent: Dec. 5, 1989

[54] PROCESS FOR THE PREPARATION OF BENZOTRIFLUORIDES WHICH ARE SUBSTITUTED BY FLUORINE AND OPTIONALLY IN ADDITION BY CHLORINE

[75] Inventors: Albrecht Marhold, Leverkusen; Rudolf Braden, Odenthal, both of Fed. Rep. of Germany

[73] Assignee: Bayer Aktiengesellschaft, Leverkusen, Fed. Rep. of Germany

[21] Appl. No.: 220,038

[22] Filed: Jul. 15, 1988

[30] Foreign Application Priority Data

Aug. 3, 1987 [DE] Fed. Rep. of Germany ....... 3725659

[51] Int. Cl.$^4$ .............................................. C07C 21/24
[52] U.S. Cl. ................................................... 570/144
[58] Field of Search ........................................ 570/144

[56] References Cited

U.S. PATENT DOCUMENTS

| 3,359,336 | 12/1967 | Tiganik | 570/204 |
| 4,351,978 | 9/1982 | Yasuhiro Hatano et al. | 585/469 |
| 4,590,315 | 5/1986 | Maul et al. | 570/127 |

FOREIGN PATENT DOCUMENTS 1067412  5/1967  United Kingdom .

OTHER PUBLICATIONS

Chemical Abstracts, vol. 87, No. 17, Oct. 24, 1977, Columbus, Oh., V. E. Platonov et al. "Thermolytic Reactions of polyfluoro-organic compounds XIX. Reaction of decafluorobiphenyl and octa-fluoronaphthalene With Potassium fluoride and poly(tetrafluoro--ethylene)" pp. 685, Zusammenfassung-No. 134 761d. Izv. Sib. Otd. Akad. Nauk SSSR, Ser. Khim, Nauk 1977, (2), 133-141 Chemical Abstracts, Tenth Collective Index (1977-1981), Formulas $C_6H_5$—$C_8H_{24}N_4ZN$, pg. 225F, Formel $C_7HF_7$, erstgenannte Verbindung.

Primary Examiner—Donald B. Moyer
Assistant Examiner—T. S. Hanna
Attorney, Agent, or Firm—Sprung Horn Kramer & Woods

[57] ABSTRACT

Benzotrifluorides substituted by fluorine and optionally in addition by chlorine, some of which are new, are prepared by hydrogenating benzotrifluorides which are substituted by fluorine and chlorine, in the presence of a catalyst and a hydrogen chloride acceptor.

13 Claims, No Drawings

PROCESS FOR THE PREPARATION OF BENZOTRIFLUORIDES WHICH ARE SUBSTITUTED BY FLUORINE AND OPTIONALLY IN ADDITION BY CHLORINE

The present invention relates to a process for the preparation of benzotrifluorides which are substituted by fluorine and optionally in addition by chlorine by selectively hydrogenating benzotrifluorides which contain fluorine and chlorine, and to new benzotrifluorides accessible in this way.

To date, fluorinated benzotrifluorides have generally been prepared from chlorobenzotrifluorides by replacing the chlorine of the latter by fluorine for example, using potassium fluoride, (see G. Fuller, J. Chem. Soc. 1965. 6264; J. P. Kolenko et al., Zh. Obsch. Khim. 37. 1686 (1967) and EP-A-34,402). In a chlorine/fluorine exchange of this type, the activated chlorine atoms in the o- and p-position relative to the $CF_3$ group can be replaced relatively easily, while the Cl atoms in m-position can be replaced by fluorine only with great difficulty. A certain pattern of the fluorine substituents in the desired product thus requires that corresponding chloine compounds are available. However, the chlorination of benzotrifluoride proceeds by an equation which is determined by the influencing action of the $CF_3$ group and which, in some cases, renders it impossible to obtain certain substitution patterns (see A. H. Ushakov et al., Zh, Organ. Khim. 12, 2204 (1976) and 20, 2187 (1984)). These include, for example, 2,4,6-trichlorobenzotrifluoride and 2,3,4,6-tetrachlorobenzotrifluoride. There is therefore still a demand for a simple process for the preparation of fluorinated benzotrifluorides which avoids these difficulties.

A process has not been found for the preparation of benzotrifluorides which are substituted by fluorine and optionally in addition by chlorine which is characterized in that benzotrifluorides containing fluorine and chlorine are hydrogenated in the presence of a catalyst and in the presence of a hydrogen chloride acceptor.

In the process according to the invention, benzotrifluorides which contain fluorine and chlorine and which correspond to the formula (I)

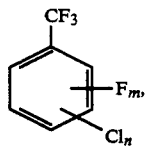

in which
  m stands for an integer from 1 to 4 and
  n stands for an integer from 1 to 5−m
can, for example, be employed.

The starting benzotrifluorides preferably contain 2 to 4 fluorine atoms and 1 to 2 chlorine atoms. The chlorine atoms in these compounds are preferably in the ortho or meta position relative to the $CF_3$ group, particularly preferably in the meta position. Particularly preferred starting benzotrifluorides are 2,3,4,6-tetrafluoro-5-chlorobenzotrifluoride, 2,4,6-trifluoro-3,5-dichlorobenzotrifluoride, 2,4-difluoro-3,5-dichlorobenzotrifluoride, 3,4-difluoro-5-chlorobenzotrifluoride, 2,3,4-trifluoro-5-chlorobenzotrifluoride, 4,5-difluoro-2-chlorobenzotrifluoride, 2,4-difluoro-5-chlorobenzotrifluoride and 2,4-difluoro-3-chlorobenzotrifluoride.

Suitable initial benzotrifluorides for the process according to the invention can be prepared, for example, by firstly chlorinating benzotrifluoride and then replacing some of the chlorine atoms introduced by fluorine atoms by reaction with potassium chloride (see, for example, G. Fuller, J. Chem. Soc. 1965, 6264, J. P. Kolenko et al., Zh. Obsch. Khim. 37, 1686 (1967) and EP-A-34,402).

Suitable catalysts are hydrogenated catalysts known in principle, for example those which contain elements of the subgroup VIII of the periodic table in the form of metals or in the form of compounds. Particularly suitable are nickel, platinum, palladium and their compounds, for example in the form of Raney nickel, metallic platinum, metallic palladium and palladium tetra-(triphenylphosphine). It is also possible for the catalytically-active substance to be applied to support materials, for example to activated charcoal, silica, alumina, silicates or alkaline earth metal sulphates.

Preferred catalysts are Raney nickel and metallic palladium on activated charcoal.

Alternatively, the catalysts can consist of several components and can, for example, also contain promoters, which may also be elements and compounds other than those of the metals of the subgroup VIII of the periodic table The amount of catalyst is generally not crucial. For example, it can be 0.01 to 15% by weight relative to the employed benzotrifluoride. Preferably, this amount is 0.1 to 10% by weight. "Catalyst" is taken to mean the active catalyst, hence in the case of support catalysts only the active metal.

The hydrogenation is generally carried out in the presence of solvents or diluents. It is not absolutely necessary for these to be capable of completely dissolving the materials employed, since it is also possible for a two-phase substrate to be hydrogenated. For example, the starting benzotrifluoride and/or the hydrogen chloride acceptor can be present partly or completely in suspended form during hydrogenation. Suitable solvents and diluents are, for example, organic acids, such as acetic acid; alcohols, such as methanol, ethanol, propanol and isopropanol; ethers, such as tetrahydrofuran; nitriles, such as acetonitrile, and water.

Suitable hydrogen chloride acceptors are a wide variety of inorganic and organic bases, for example, the hydroxides, carbonates, acetates and ammonium salts of the alkali metals and alkaline earth metals, and amines, in particular tertiary amines. Sodium acetate, triethylamine, N,N-dimethylaniline, pyrimidine and picoline are preferred.

The hydrogen chloride acceptor can be employed in various amounts. Preferably, at least 0.8 equivalent of hydrogen chloride acceptor is employed per equivalent of chlorine atoms to be eliminated from the benzotrifluoride employed.

If it is intended that all the chlorine atoms present be eliminated from the benzotrifluoride employed, the upper limit for the amount the hydrogen chloride acceptor to be employed is not crucial. In this case it is for practical reasons generally advantageous to employ not more than 2 equivalents of hydrogen chloride acceptor per equivalent of chlorine atoms to be eliminated.

If it is not intended that all of the chlorine atoms present in the benzotrifluoride employed be eliminated, i.e., if it is intended to prepare benzotrifluorides which still contain chlorine atoms, then one should not employ considerably more hydrogen chloride acceptor than is stoichiometrically required. In this case, preferably up to 1.2, particularly preferably up to 1.05 and very particularly preferably 1 equivalent of hydrogen chloride acceptor are, or is, employed per equivalent of chlorine atoms to be eliminated.

The hydrogenation according to the invention can, for example, be carried out at pressures in the range from atmospheric pressure to 200 bar and temperatures in the range from 20° to 200° C. Pressures in the range from atmospheric pressure to 120 bar and temperatures in the range from 50° to 140° C. are preferred.

In the case of complete dechlorination of the starting material, the reaction according to the invention is complete when hydrogen is no longer taken up, and, in the case of selective dechlorination, when the amount of hydrogen required stoichiometrically has been taken up.

Working up of the reaction mixtures can be carried out in a simple manner. For example, the procedure can be such that, firstly, the solid constituents of the reaction mixture (in general, this is the catalyst, where appropriate, also, for example, the loaded hydrogen chloride acceptor) are removed by filtration and the prepared benzotrifluoride, which is substituted by fluorine and optionally in addition by chlorine, is obtained from the filtrate by distillation.

The benzotrifluoride obtained contains at least 1 chlorine atom less than the starting benzotrifluoride. For example, the benzotrifluoride prepared can be a product of the formula (II)

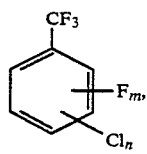
(II)

in which
m' stands for an integer from 1 to 4 and
n' stands for zero or an integer up to 4−m'.

The process according to the invention has the advantage that very pure products are obtained in good yields. The starting compounds are easily accessible because the replacement of chlorine by fluorine proceeds more readily in higher-chlorinated benzotrifluorides than in lower-chlorinated benzotrifluorides. The route according to the invention to give benzotrifluorides which are substantially by fluorine and optionally by chlorine is therefore more advantageous than the direct introduction of fluorine into unsubstituted benzotrifluorides. Moreover, fluorine-substituted and optionally chlorine-substituted benzotrifluorides having substitution patterns which hitherto were not accessible, or only accessible with difficulty, can be obtained.

In the process according to the invention, it is surprising that the fluorine substitutents present on the aromatic ring are not eliminated and also that virtually no hydrogenation of the aromatimc ring takes place. Moreover, it is surprising that if several chlorine substituents are present in the starting material, these can be eliminated individually with good selectivities.

The present invention furthermore relates to fluorine-substituted benzotrifluorides of the formula (III)

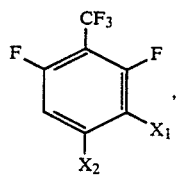
(III)

in which
$X_1$ stands for fluorine or chlorine and
$X_2$, in the case of $X_1$=fluorine, stands for hydrogen or fluorine, and, in the case of $X_1$=chlorine, for fluorine.

The benzotrifluorides of the formula (III) are, in particular, 2,3,4,6-tetrafluorobenzotrifluoride, 2,4,6-trifluoro-3-chlorobenzotrifluoride and 2,3,6-trifluorobenzotrifluoride.

The benzotrifluorides of the formula (III) can be prepared as described above.

Benzotrifluorides which are substituted by fluorine and optionally by chlorine are important intermediates in the preparation of active compounds. For example, benzotrifluorides which are substituted by fluorine and optionally by chlorine and which can be obtained according to the present invention can be reacted with hydrazine hydrate, and the aryl hydrazines obtainable in this reaction can be reacted with 1,3-diketones of the formula (IV)

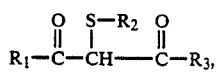
(IV)

in which
$R_1$ and $R_3$ stand for alkyl and
$R_2$ stands for alkyl or halogenoalkyl,
and 3,5-dialkyl-1-aryl-pyrazoles of the formula (V)

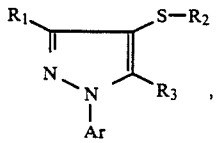
(V)

in which
$R_1$ to $R_3$ have the meaning given in formula (IV) and
Ar stands for a fluorinated and optionally chlorinated benzotrifluoride radical
can thus be obtained.

From compounds of the formula (V), compounds of the formula (VI)

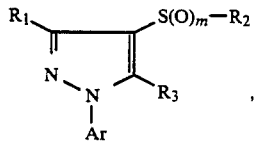
(VI)

in which
$R_1$ to $R_3$ and Ar have the meaning given in formula (V) and
m stands for 1 or 2
can be parepared by oxidation in a customary manner.

The compounds of the formulae (V) and (VI) are distinguished by a strong insecticidal action, for example against insects which are harmful to plants, such as the larvae of the mustard beetle. They also have a strong action against hygiene and stored-product pests, such as the common house fly (Musca domestica) and against parasites of warm-blooded animals, such as the autumn fly (Musca autumnalis).

EXAMPLES

Example 1

1 mol of starting material in 1 l of acetic acid together with 1.05 mol of sodium acetate per mol of chlorine to be eliminated were initially introduced into a hydrogenation apparatus. 10 g of catalyst (5% by weight of metallic palladium on activated charcoal) were then added, and the mixture was subsequently hydrogenated at a hydrogen pressure of 30 to 50 bar at 120° C. until the pressure remained constant. The catalyst was then separated from the reaction mixture by filtration, and the filtrate was distilled via a column. The distillate was washed with water in order to remove small amounts of acetic acid. The reaction product had a purity of more than 98% in each case. Further details can be seen from Table 1.

TABLE 1

| Example No. | Starting material (... benzotrifluoride) | Product (... benzotrifluoride) | Boiling point at 1013 mbar | Refractive index $n_D^{20}$ | Yield % of theory |
|---|---|---|---|---|---|
| 1a | 5-Chlorotetrafluoro- | 2,3,4,6-Tetrafluoro- | 105–106° C. | 1.3770 | 92 |
| 1b | 3,5-Dichlorotrifluoro- | 2,4,6-Trifluoro- | 104° C. | 1.3840 | 83 |
| 1c | 3,5-Dichlorotrifluoro- | 3-Chloro-2,4,6-trifluoro- | 145° C. | 1.4170 | 76 |
| 1d | 3,5-Dichloro-2,4-difluoro- | 2,4-Difluoro- | 105–106° C. | 1.3968 | 84 |
| 1e | 5-Chloro-3,4-difluoro- | 3,4-Difluoro- | 103–104° C. | 1.3958 | 85 |
| 1f | 5-Chloro-2,3,4-trifluoro- | 2,3,4-Trifluoro- | 105–106° C. | 1.3842 | 89 |
| 1g | 3-Chloro-2,5,6-trifluoro- | 2,3,6-Trifluoro- | 105–107° C. | 1.3850 | 82 |

Example 2

216 g (1 mol) of 2-chloro-4,5-difluorobenzotrifluoride in 1 l of methanol were initially inroduced into a hydrogenation apparatus, and 110 g of triethylamine and 15 g of Raney nickel were added. The hydrogenation apparatus was then flushed using hydrogen and then warmed to 80° C., and a pressure of 100 bar of hydrogen was applied. After the hydrogen pressure had dropped, it was restored again to 100 bar, and the mixture was allowed to react until the pressure remained constant. After cooling, the pressure was released, and the reaction mixture was filtered. The filtrate was diluted using 3 l of water, and the organic phase was separated off. The latter was dried and distilled via a column. 147 g of 3,4-difluorobenzotrifluoride having a boiling point of 108° to 109° C. at 1013 mbar and a refractive index $n_D^{20}$ of 1.3973 were obtained.

Example 3

The procedure as in Example 2 was followed, but 1 mol of 5-chloro-2,4-difluorobenzotrifluoride was employed, and 151 g of 2,4-difluorobenzotrifluoride having a boiling point of 105° to 106° C. at 1013 mbar and a refractive index $n_D^{20}$ of 1.3970 were obtained.

Example 4

100 g of 3-chloro-2,4-difluorobenzotrifluoride in 500 ml of acetonitrile and 60 g of pulverulent sodium carbonate were initially introduced into a hydrogenation apparatus equipped with a diffuser stone and a stirrer. 10 g of catalyst (5% by weight of metallic palladium on activated charcoal) were then added, and hydrogen was passed in at 80° C. for 10 hours. Subsequently, the batch was cooled and filtered, and the filtrate was distilled via a column packed with perforated rings made of stainless steel. 56 g of 2,4-difluorobenzotrifluoride having a boiling point of 105° to 106° C. at 1,030 mbar were obtained. The refractive index $n_D^{20}$ was 1.3968.

Example 5

300 g of 3,5-dichloro-2,6-difluorobenzotrifluoride in 1,200 ml of acetic acid and 210 g of sodium acetate were initially introduced into a hydrogenation apparatus, 10 g of 5% palladium on A-charcoal were added, and the batch was hydrogenated at a hydrogen pressure of 30 to 50 bar at 80°–120° C., after the apparatus has been flushed with hydrogen. After the hydrogen uptake had ended (constant pressure), the batch was cooled, the catalyst was filtered off by suction, and the solution was stirred with 2 l of water. The organic phase which separated was removed and distilled. Boiling point: 106°–107° C.; $n_D^{20}$: 1.3972; yield 193 g of 2,6-difluorobenzotrifluoride.

What is claimed is:

1. A process for the preparation of benzotrifluoride substituted by fluorine and optionally in addition by chlorine, comprising hydrogenating a benzotrifluoride substituted by fluorine and chlorine in the presence of a hydrogenation catalyst and in the presence of a hydrogen chloride acceptor and in an inert diluent or solvent, wherein the benzotrifluoride is of the formula (I)

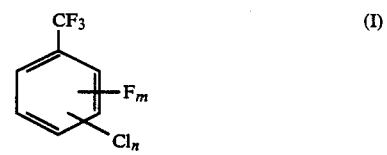

in which
  m is an integer of 1 to 4 and
  n is an integer from 1 to 5−m,
and recovering the benzotrifluoride product.

2. A process according to claim 1, in which the catalyst contains an element of the subgroup VIII of the periodic table in the form of a metal or in the form of a compound.

3. A process according to claim 1, in which the hydrogen chloride acceptor is a hydroxide, carbonate, acetate or an ammonium salt of an alkali metal or alkaline earth metal.

4. A process according to claim 1, wherein the hydrogen chloride acceptor is an amine.

5. A process according to claim 1, in which at least 0.8 equivalent of hydrogen chloride acceptor is employed per equivalent of chlorine atoms to be eliminated.

6. A process according to claim 1, in which the hydrogenation is carried out at a pressure in the range from atmospheric pressure to 200 bar and at a temperature in the range from 20° C. to 200° C.

7. A process according to claim 1, wherein the benzotrifluoride is 2,3,4,6-tetrafluoro-5-chlorobenzotrifluoride, 2,4,6-trifluoro-3,5-dichlorobenzotrifluoride, 2,4-difluoro-3,5-dichlorobenzotrifluoride, 3,4-difluoro-5-dichlorobenzotrifluoride, 2,3,4-trifluoro-5-chlorobenzotrifluoride, 4,5-dichloro-2-chlorobenzo-trifluoride, 2,4-difluoro-5-chlorobenzotrifluoride or 2,4-difluoro-3-chlorobenzotrifluoride.

8. A process according to claim 2, wherein the catalyst comprises nickel, platinum or palladium.

9. A process according to claim 8 wherein the catalyst comprises Raney nickel, metallic platinum, metallic palladium or palladium tetra-(triphenylphosphine).

10. A process according to claim 1, wherein 0.01 to 15% by weight catalyst is employed relative to the benzotrifluoride employed.

11. A process according to claim 1, wherein 0.1 to 10% by weight catalyst is employed relative to the benzotrifluoride employed.

12. A process according to claim 1, wherein the diluent or solvent is an organic acid, an alcohol, an ether, a nitrile or water.

13. A process according to claim 1, wherein the reaction mixture consists essentially of said benzotrifluoride of the formula (I), a hydrogenation catalyst, a hydrogen chloride acceptor and an inert diluent or solvent.

* * * * *